(12) United States Patent
Sloot

(10) Patent No.: US 7,393,336 B2
(45) Date of Patent: Jul. 1, 2008

(54) BAND WITH HIDDEN POCKET

(75) Inventor: Alexander Sloot, Sugarloaf, PA (US)

(73) Assignee: Printwork Industries, Inc., Hazleton, PA (US)

( * ) Notice: Subject to any disclaimer, the term of this patent is extended or adjusted under 35 U.S.C. 154(b) by 185 days.

(21) Appl. No.: 11/415,920

(22) Filed: May 1, 2006

(65) Prior Publication Data

US 2007/0270731 A1 Nov. 22, 2007

(51) Int. Cl.
*A61F 13/00* (2006.01)
(52) U.S. Cl. .............................. 602/60; 602/61; 602/75
(58) Field of Classification Search ............. 602/60–64, 602/75–79, 19; 607/112; 2/16, 170, 22, 2/339, 340, 123, 321, 216; 224/164–171, 224/219–222; D3/215, 218, 224, 226
See application file for complete search history.

(56) References Cited

U.S. PATENT DOCUMENTS

| | | | | |
|---|---|---|---|---|
| D287,229 S | * | 12/1986 | Hallman et al. ................. D11/5 |
| 5,002,212 A | * | 3/1991 | Charleton ................... 224/221 |
| 5,158,541 A | * | 10/1992 | McCurley ..................... 602/79 |
| D373,900 S | | 9/1996 | Montgomery, Sr. .......... D3/226 |
| 5,671,481 A | | 9/1997 | Giard ............................. 2/170 |
| 6,056,711 A | * | 5/2000 | Domanski et al. ............. 602/18 |
| 6,227,424 B1 | | 5/2001 | Roegner ..................... 224/219 |
| 6,443,341 B1 | | 9/2002 | Rittmann .................... 224/219 |
| 6,807,680 B2 | * | 10/2004 | Sloot ............................... 2/16 |

* cited by examiner

*Primary Examiner*—Kim M Lewis
(74) *Attorney, Agent, or Firm*—St. Onge Steward Johnston & Reens LLC

(57) ABSTRACT

A band adapted to be worn on a limb of a person or animal includes a fabric member and an elastic member attached to the fabric member. A first half of a fastening system is attached to an inner surface of the elastic member, and a second half of the fastening system is attached to the fabric member on the outer surface thereof only around a portion of its perimeter so as to define a space between the outer surface of the fabric member and the second half of the fastening system, the space adapted to be used as a pocket. The band is adjustable to accommodate limbs of various sizes by adjusting a position along the second half of the fastening system where the first half of the fastening system is detachably connected.

10 Claims, 4 Drawing Sheets

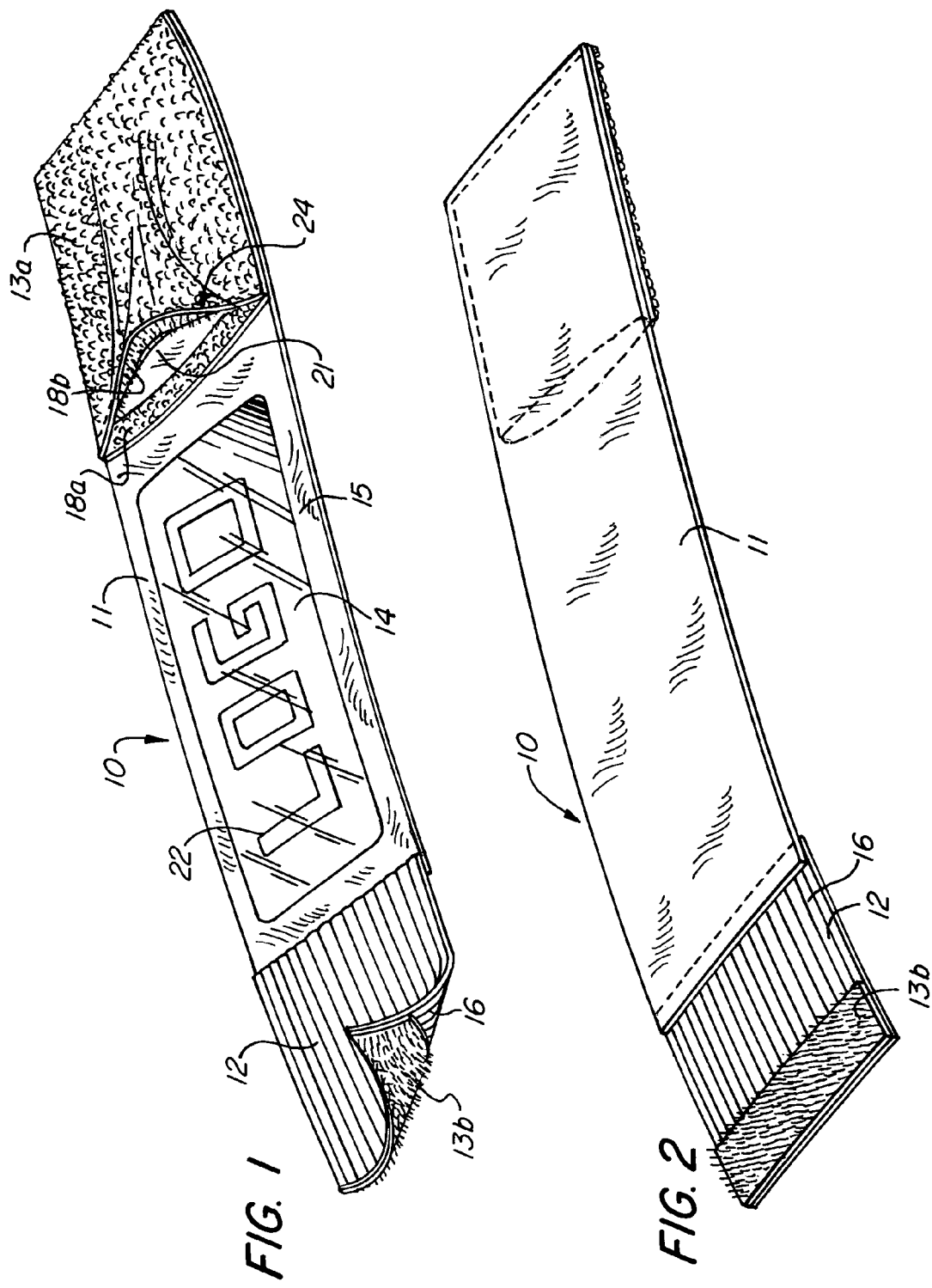

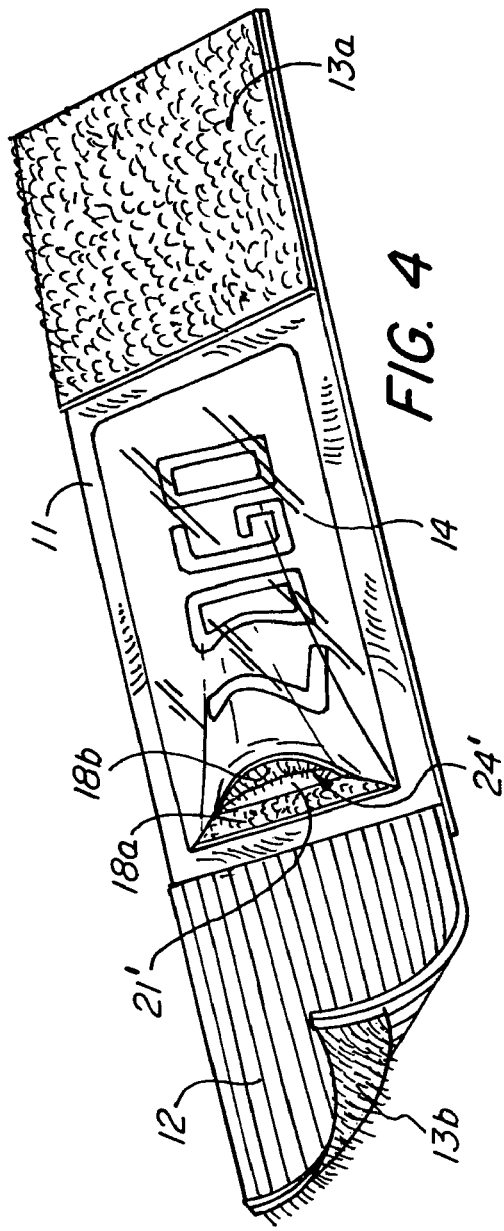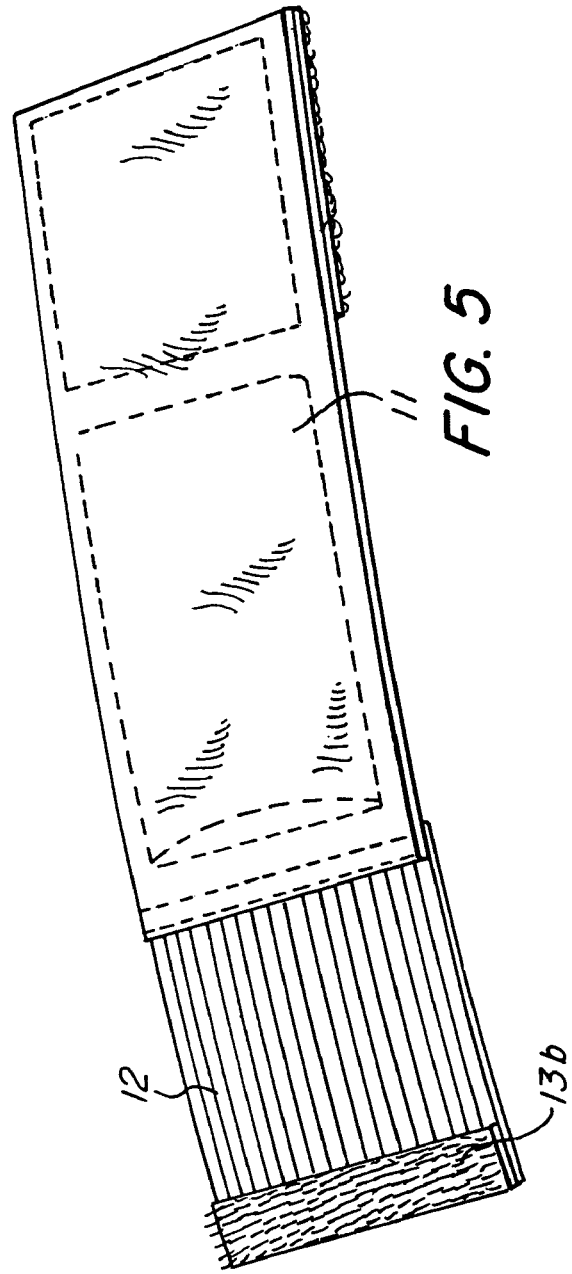

BAND WITH HIDDEN POCKET

FIELD OF THE INVENTION

The present invention relates to a band to be worn by a person or animal for identification and/or safety purposes, for containing articles within a hidden pocket, and which may be quickly and easily adjusted for use on limbs having various dimensions.

BACKGROUND OF THE INVENTION

Bands which are worn on the limb of a person or animal are widely used to serve various functions. For example, bands on the arm, wrist, leg, or ankle have been used to allow easy identification of the wearer, to increase the wearer's visibility in certain conditions, and to carry articles. Nevertheless, there are deficiencies in this general area in that no bands satisfactorily perform all of these functions.

In general, bands are used most often by people engaged in an activity that requires the use of both hands or where having both hands free is preferred, for example, during exercise activities. In these situations, a person often desires to carry small articles such as keys, money, and/or identification. In cases when an activity is performed near automobile traffic, a person often desires to wear reflective material that will make him or her highly visible in an automobile's headlights. Additionally, for some organized sporting events, such as marathons and other races, it is necessary to provide the participants with lightweight, unobtrusive means of identification. Ideally, all of these ends could be achieved by a single band.

U.S. Pat. No. 5,671,481 to Giard discloses a wristband consisting of moisture-absorbent material with a pocket for carrying small articles. The wristband is composed of two, three, or more plies of fabric. The pocket is formed between two of these plies of fabric. The band is folded along its long dimension and has fasteners at two ends to provide for connecting the ends and wearing around the wrist. Due to its design, however, this wristband suffers from limited adjustability. Because it is composed of fabric that is not elastic, the wrist band will not be able to be worn on the upper arm or leg. Also, the wristband disclosed in Giard is relatively complex in design and appears to be disadvantageously difficult to don.

Many other US Patents involve means for including a pocket on a band of some kind, for example U.S. Pat. No. 6,443,341 to Rittmann, U.S. Pat. No. 6,227,424 to Roegner, and U.S. Pat. No. D373,900 to Montgomery, Sr. However, all of these designs suffer from the disadvantage of excessive complexity in creating the pocket structure. Many also involve relatively expensive components such as zippers or snap fasteners. These things contribute to the overall size and weight of the band. Because bands are most often used during exercise activities, it is important that the size and weight of the band be minimized so as to interfere with the wearer as little as possible.

What is desired, therefore, is a band to be worn by a person or animal that is highly adjustable for use on limbs of various sizes, that allows the wearer to easily carry small articles, that is lightweight, of minimal size and bulk, that permits the application of reflective material and/or an identification placard, and that is simple in design and easy to produce.

SUMMARY OF THE INVENTION

Accordingly, it is an object of the present invention to provide a band to be worn by a person or animal for identification and/or safety purposes, for carrying small articles, and which will fit on limbs of substantially all sizes.

Another object of the present invention is to provide a band having the above characteristics and which is of minimal size and weight.

A further object of the present invention is to provide a band having the above characteristics and which is easy to don without the help of others.

Yet another object of the present invention is to provide a band having the above characteristics and which is relatively simple in design and inexpensive to produce.

These and other objects of the present invention are achieved in accordance with one embodiment of the present invention by a band adapted to be worn on a limb of a person or animal. The band includes a fabric member having a length and a width and having a first longitudinal end and a second longitudinal end, the fabric member having an inner surface which is soft and not abrasive to human skin and an outer surface. An elastic member, includes a first longitudinal end and a second longitudinal end, with the first longitudinal end of the elastic member being attached to the fabric member adjacent to the second longitudinal end thereof, the elastic member having a length parallel to the length of the fabric member, and being expandable along its length. A first half of a first fastening system is attached to an inner surface of the elastic member at the second longitudinal end thereof, and a second half of the first fastening system is attached to the fabric member on the outer surface thereof only around a portion of its perimeter so as to define a space between the outer surface of the fabric member and the second half of the first fastening system, the space adapted to be used as a pocket. The band is adjustable to accommodate limbs of various sizes by adjusting a position along the second half of the first fastening system where the first half of the first fastening system is detachably connected.

In some embodiments, the fabric member is generally rectangular in shape. In certain of these embodiments, the second half of the first fastening system is generally rectangular in shape, and the second half of the first fastening system is attached to the fabric member along three of four edges. In certain embodiments, the elastic member is generally rectangular in shape. In other embodiments, the band is made totally of an elasticized material. In yet other embodiments, not only is the band made of an elasticized material, but of an absorbent elasticized material, such as terrycloth.

In some embodiments, the first half of the first fastening system comprises one of a hook portion or a loop portion of a hook-and-loop fastening system and the second half of the first fastening system comprises the other of a hook portion or a loop portion of a hook-and-loop fastening system. In some embodiments, the band further includes a second fastening system having a first half attached to an inner surface of the second half of the first fastening system adjacent an opening of the pocket and a second half attached to the outer surface of the fabric member adjacent the opening of the pocket to detachably close the pocket. In certain of these embodiments, the first half of the second fastening system comprises one of a hook portion or a loop portion of a hook-and-loop fastening system and the second half of the second fastening system comprises the other of a hook portion or a loop portion of a hook-and-loop fastening system.

In some embodiments, the band further includes an appliqué attached to the outer surface of the fabric member. In certain of these embodiments, the appliqué is formed from a material selected from the group consisting of a reflective material, a glow-in-the-dark material, a non-reflective vinyl with a multi-color decoration, an embroidery, a direct screen print, a heat applied transfer, a fabric material, and combinations of these. In certain embodiments, the appliqué includes a logo printed thereon or formed therein.

In accordance with another embodiment of the present invention, a band adapted to be worn on a limb of a person or animal includes a fabric member having a length and a width and having a first longitudinal end and a second longitudinal end, the fabric member having an inner surface which is soft and not abrasive to human skin. An appliqué is attached to the fabric member on the outer surface thereof only around a portion of its perimeter so as to define a space between the appliqué and the fabric member, the space adapted to be used as a pocket. A first fastening system includes a first half attached to an inner surface of the appliqué adjacent an opening of the pocket and a second half attached to the outer surface of the fabric member adjacent the opening of the pocket to detachably close the pocket. An elastic member has a first longitudinal end and a second longitudinal end, with the first longitudinal end attached to the fabric member adjacent to the second longitudinal end thereof, the elastic member having a length parallel to the length of the fabric member, and being expandable along its length. A first half of a second fastening system is attached to an inner surface of the elastic member at the second longitudinal end thereof, and a second half of the second fastening system is attached to the fabric member on the outer surface thereof at the first longitudinal end thereof. The band is adjustable to accommodate limbs of various sizes by adjusting the position along the second half of the second fastening system where the first half of the second fastening system is detachably connected.

In some embodiments, the fabric member is generally rectangular in shape. In certain of these embodiments, the appliqué is generally rectangular in shape, and the appliqué is attached to the fabric member along three of four edges. In certain embodiments, the elastic member is generally rectangular in shape. In some embodiments, the first half of the first fastening system comprises one of a hook portion or a loop portion of a hook-and-loop fastening system and the second half of the first fastening system comprises the other of a hook portion or a loop portion of a hook-and-loop fastening system. In some embodiments, the first half of the second fastening system comprises one of a hook portion or a loop portion of a hook-and-loop fastening system and the second half of the second fastening system comprises the other of a hook portion or a loop portion of a hook-and-loop fastening system.

In some embodiments, the appliqué is formed from a material selected from the group consisting of a reflective material, a glow-in-the-dark material, a non-reflective vinyl with a multi-color decoration, an embroidery, a direct screen print, a heat applied transfer, a fabric material, and combinations of these. In some embodiments, the appliqué includes a logo printed thereon or formed therein.

In accordance with a further embodiment of the present invention, a band adapted to be worn on a limb of a person or animal includes a first elastic member arranged as a continuous ring-shaped band and a second elastic member, which is preferably generally flat, attached to the first elastic member only around a portion of its periphery so as to define a space between the first elastic member and the second elastic member with an opening for accessing the space, the space adapted to be used as a pocket. A hook-and-loop fastening system is provided for detachably closing the opening of the pocket, the hook-and-loop fastening system comprising a first portion attached to an outer surface of the first elastic member and a second portion attached to an inner surface of the second elastic member.

In some embodiments, the first elastic member is formed as an elongated member which is wrapped into a ring shape with ends thereof fastened together along a seam. In some embodiments, the second elastic member is generally rectangular in shape, and the second elastic member is attached to the first elastic member along three of its edges. In some embodiments, the second elastic member is attached to the first elastic member on an inner surface of the first elastic member.

In some embodiments, the band further includes an appliqué applied to an outer surface of the band. In certain of these embodiments, the appliqué is formed from a material selected from the group consisting of a reflective material, a reflective material with a single or multi-color print, a glow-in-the-dark material, a non-reflective vinyl with a multi-color decoration, an embroidery, a direct screen print, a heat applied transfer, a fabric material, and combinations of these. In certain embodiments, the appliqué includes a logo printed thereon or formed therein.

The invention and its particular features and advantages will become more apparent from the following detailed description considered with reference to the accompanying drawings.

BRIEF DESCRIPTION OF THE DRAWINGS

FIG. 1 is an isometric top view of a band in accordance with an embodiment of the present invention.

FIG. 2 is an isometric bottom view of the band of FIG. 1.

FIG. 4 is an isometric top view of another embodiment of a band in accordance with the present invention.

FIG. 5 is an isometric bottom view of the band of FIG. 4.

DETAILED DESCRIPTION OF THE DRAWINGS

Figure 3:
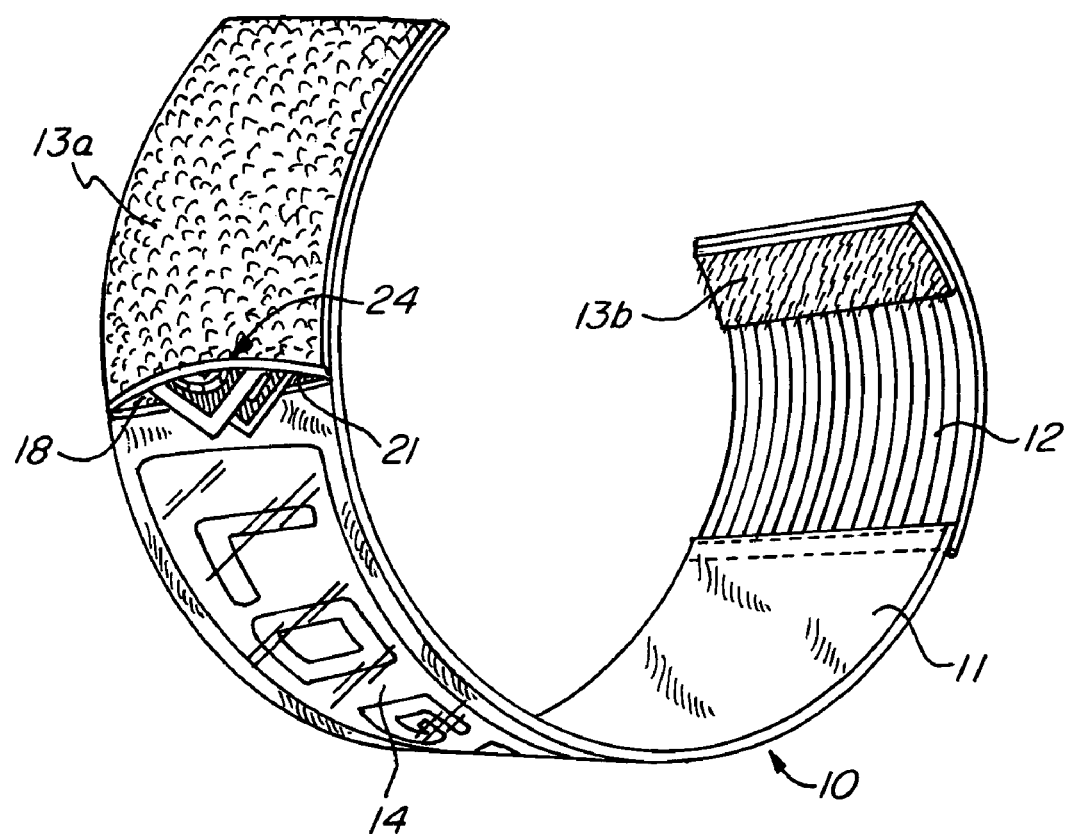
FIG. 3 is a perspective view of the band of FIG. 1 as it would wrap around a wearer's arm.

Referring first to FIGS. 1, 2, and 3, a band 10 to be worn by a person or animal is shown. The band 10 is designed to be worn on the limb of the person or animal, and may be worn, for example, on the upper arm, forearm wrist, thigh, calf, ankle, etc. The band 10 includes a fabric member 11 having a length and a width and an elastic member 12 having a length and a width, which is attached to a first longitudinal end of fabric member 11 such that the combined length is appropriate for wear on the limb of a person or animal. Fabric member 11 could be formed of cotton, terry-cloth, fleece, nylon, canvas, or substantially any other natural or synthetic material, in a rectangle, circle, oval, or other shape.

Attached to fabric member 11 at its second longitudinal end on its outer surface 15 is first portion 13a of fastening system 13a, 13b. Fastening system 13a, 13b is preferably composed of a hook-and-loop system, although other fastening systems may be employed. First portion 13a is attached on three of its edges by means of heat application, adhesives, sewing, ultrasonic welding, or the like. Second portion 13b of fastening system 13a, 13b is attached to the inner surface 16 of elastic member 12 by means of heat application, adhesives, sewing, ultrasonic welding, or the like, as shown in FIGs. 1 and 2. Fastening system 13a, 13b is used as shown in FIG. 3 to detachably connect the two ends of band 10 while band 10 is wrapped around the limb of a person or animal.

At the unattached edge of first portion 13a is opening 21 as shown in FIG. 1. Opening 21 provides access to the space between fabric member 11 and first portion 13a, which is adaptable to be used as a pocket 24 for carrying items. Pocket 24 is closed and sealed using a second fastening system 18a, 18b. Second fastening system 18a, 18b is preferably composed of a hook-and-loop system, although other fastening systems may be employed. First portion 18a of second fastening system 18a, 18b is attached to fabric member 11 on its outer surface by means of heat application, adhesives, sewing, ultrasonic welding, or the like. Second portion 18b of second fastening system 18a, 18b is attached to first portion 13a of first fastening system 13a, 13b on its inner surface by means of heat application, adhesives, sewing, ultrasonic welding, or the like.

FIG. 1 shows appliqué 14 attached to the outer surface of fabric member 11. Appliqué 14 may be formed of a reflective material, a glow-in-the-dark material, a non-reflective vinyl with a multi-color decoration, an embroidery, a direct screen print, a heat applied transfer, a fabric material or combinations of these. Moreover, appliqué 14 may include a corporate logo 22 printed thereon or formed therein.

In a second embodiment, shown in FIGS. 4 and 5, pocket 24' is located between appliqué 14 and fabric member 11. Appliqué 14 is attached on only three of its edges to fabric member 11. Appliqué 14 may again be formed of a reflective material, a glow-in-the-dark material, a non-reflective vinyl with a multi-color decoration, an embroidery, a direct screen print, a heat applied transfer, a fabric material or combinations of these. Thus, there is an opening 21' at the unattached edge which provides access to pocket 24'. Pocket 24' can be closed and sealed in this embodiment in a similar fashion as the first embodiment, using a second fastening system 18a, 18b, such as a hook-and-loop fastening system, at the unattached edge of appliqué 14.

The second embodiment may also be held in place on the wearer's arm by fastening system 13a, 13b, such as in the first described embodiment. An elastic member 12 may also be used to provide fit adjustability.

Figure 6:
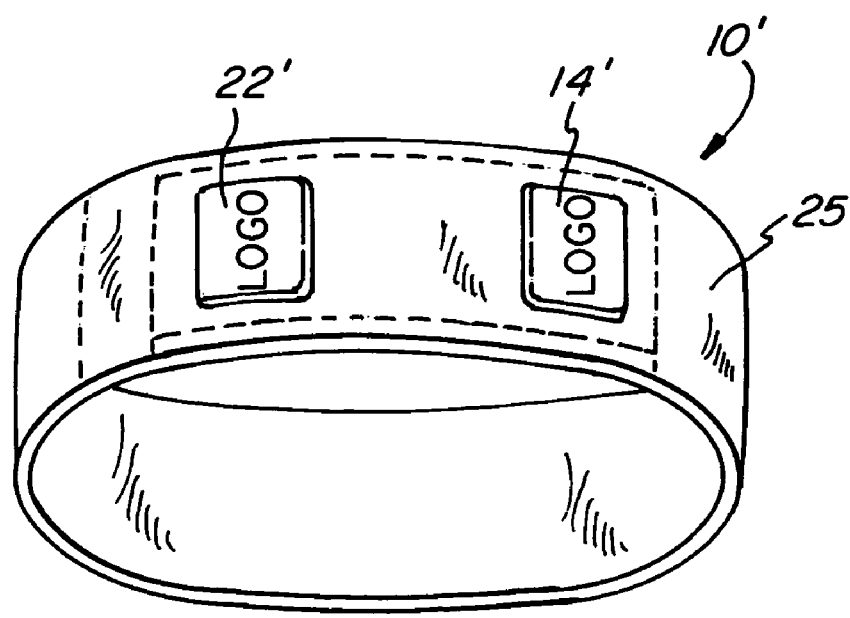
FIG. 6 is an isometric view of another embodiment of a band in accordance with the present invention.
Figure 7:
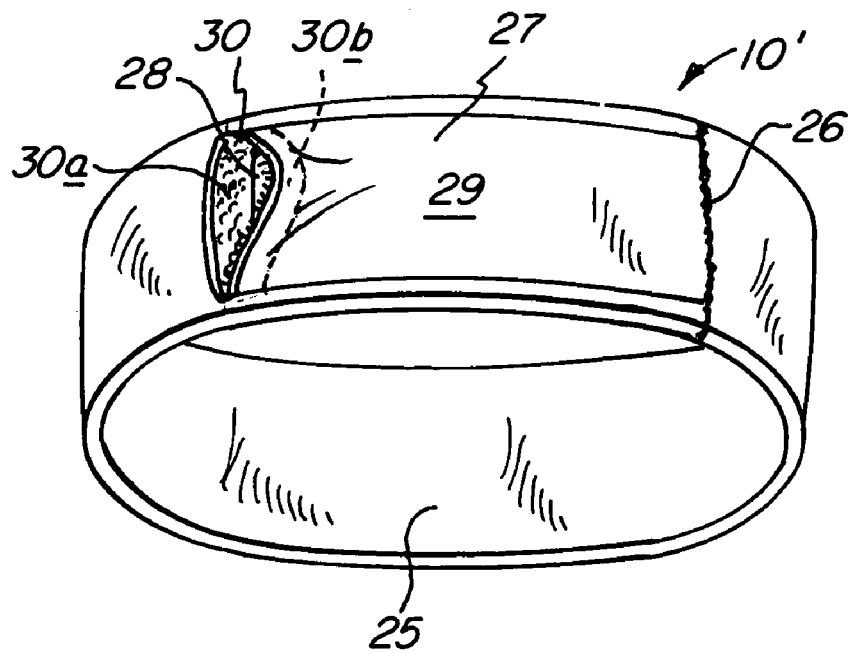
FIG. 7 is an isometric view of the band of FIG. 6 shown with the band turned inside-out.

In a third embodiment, shown in FIGS. 6 and 7, band 10' includes a first elastic member 25 which is arranged as a continuous ring-shaped band. First elastic member 25 may be formed of an elastic cotton, terry-cloth, fleece, nylon, canvas, or substantially any other natural or synthetic material, so long as the material exhibits elastic properties in order to be stretched over various body parts and be positioned and held on the desired body part. For example, when band 10' is adapted to be used as a wristband, first elastic member 25 must be sized and suitably elastic enough to fit over then hand of the wearer, yet be snug enough to be comfortably held on the wearer's wrist. First elastic member 25 may itself be formed as a continuous ring-shaped member, or it may be formed as an elongated member which is wrapped into a ring shape and the ends fastened together along a seam 26 by means of heat application, adhesives, sewing, ultrasonic welding, or the like.

Band 10' also includes a second elastic member 27, which is preferably generally flat and rectangular in shape. Second elastic member 27 is attached to first elastic member 25 on three of its edges by means of heat application, adhesives, sewing, ultrasonic welding, or the like. Second elastic member 27 may be attached to first elastic member 25 on an inner surface thereof (as shown in FIGS. 6 and 7), or an outer surface thereof. Preferably, second elastic member 27 is formed from the same material as is first elastic member 25.

At the unattached edge of second elastic member 27 is opening 28 as shown in FIG. 7. Opening 28 provides access to the space between first elastic member 25 and second elastic member 27, which is adaptable to be used as a pocket 29 for carrying items. Pocket 29 is closed and sealed using a fastening system 30. Fastening system 30 is preferably composed of a hook-and-loop system, although other fastening systems may be employed. First portion 30a of fastening system 30 is attached to first elastic member 25 on its outer surface by means of heat application, adhesives, sewing, ultrasonic welding, or the like. Second portion 30b of fastening system 30 is attached to second elastic member 27 on its inner surface by means of heat application, adhesives, sewing, ultrasonic welding, or the like.

FIG. 6 shows appliqué 14' attached to the outer surface of first elastic member 25. Appliqué 14' may be formed of a reflective material, a reflective material with a single or multi-color print, a glow-in-the-dark material, a non-reflective vinyl with a multi-color decoration, an embroidery, a direct screen print, a heat applied transfer, a fabric material or combinations of these. Moreover, appliqué 14' may include a corporate logo 22' printed thereon or formed therein. It should be noted that if second elastic member 27 is attached to an outer surface of first elastic member 25, appliqué 14' may be attached to an outer surface of second elastic member 27, rather than to first elastic member 25.

The present invention, therefore, provides a band to be worn by a person or animal that is highly adjustable for use on limbs of various sizes, that allows the wearer to easily carry small articles, that is lightweight, of minimal size and bulk, that permits the application of reflective material and/or an identification placard, and that is simple in design and easy to produce.

Although the invention has been described with reference to a particular arrangement of parts, features, and the like, these are not intended to exhaust all possible arrangements or features, and indeed many other modifications and variations will be ascertainable to those of skill in the art.

What is claimed is:

1. A band adapted to be worn on a limb of a person or animal, said band comprising:
   a fabric member having a length and a width and having a first longitudinal end and a second longitudinal end, said fabric member having an inner surface which is soft and not abrasive to human skin and an outer surface;
   an elastic member having a first longitudinal end and a second longitudinal end, the first longitudinal end of said elastic member attached to said fabric member adjacent to the second longitudinal end thereof, said elastic member having a length parallel to the length of said fabric member, and being expandable along its length;
   a first half of a first fastening system attached to an inner surface of said elastic member at the second longitudinal end thereof;
   a second half of the first fastening system attached to said fabric member on the outer surface thereof only around a portion of its perimeter so as to define a space between the outer surface of said fabric member and said second half of the first fastening system, the space adapted to be used as a pocket; and
   wherein said band is adjustable to accommodate limbs of various sizes by adjusting a position along said second half of the first fastening system where said first half of the first fastening system is detachably connected.

2. The band of claim 1 wherein said fabric member is generally rectangular in shape.

3. The band of claim 2 wherein said second half of the first fastening system is generally rectangular in shape, and wherein said second half of the first fastening system is attached to said fabric member along three of four edges.

4. The band of claim 2 wherein said elastic member is generally rectangular in shape.

5. The band of claim 1 wherein said first half of the first fastening system comprises one of a hook portion or a loop portion of a hook-and-loop fastening system and wherein said second half of the first fastening system comprises the other of a hook portion or a loop portion of a hook-and-loop fastening system.

6. The band of claim 1 further comprising a second fastening system comprising a first half attached to an inner surface of said second half of the first fastening system adjacent an opening of the pocket and a second half attached to the outer surface of said fabric member adjacent the opening of the pocket to detachably close the pocket.

7. The band of claim 6 wherein the first half of said second fastening system comprises one of a hook portion or a loop portion of a hook-and-loop fastening system and wherein the second half of said second fastening system comprises the other of a hook portion or a loop portion of a hook-and-loop fastening system.

8. The band of claim 1 further comprising an appliqué attached to the outer surface of said fabric member.

9. The band of claim 8 wherein the appliqué is formed from a material selected from the group consisting of a reflective material, a glow-in-the-dark material, a non-reflective vinyl with a multi-color decoration, an embroidery, a direct screen print, a heat applied transfer, a fabric material, and combinations of these.

10. The band of claim 9 wherein the appliqué includes a logo printed thereon or formed therein.

\* \* \* \* \*

UNITED STATES PATENT AND TRADEMARK OFFICE
CERTIFICATE OF CORRECTION

PATENT NO. : 7,393,336 B2 Page 1 of 1
APPLICATION NO. : 11/415920
DATED : July 1, 2008
INVENTOR(S) : Alexander Sloot It is certified that error appears in the above-identified patent and that said Letters Patent is hereby corrected as shown below:

On the Title Page, should read

Item (73) Assignee:

Printmark Industries, Inc., Hazleton, PA (US)

Signed and Sealed this

Sixteenth Day of September, 2008

JON W. DUDAS
*Director of the United States Patent and Trademark Office*